Oct. 13, 1953
E. S. BOERNER
Plant Pat. 1,222
ROSE PLANT
Filed Oct. 9, 1952
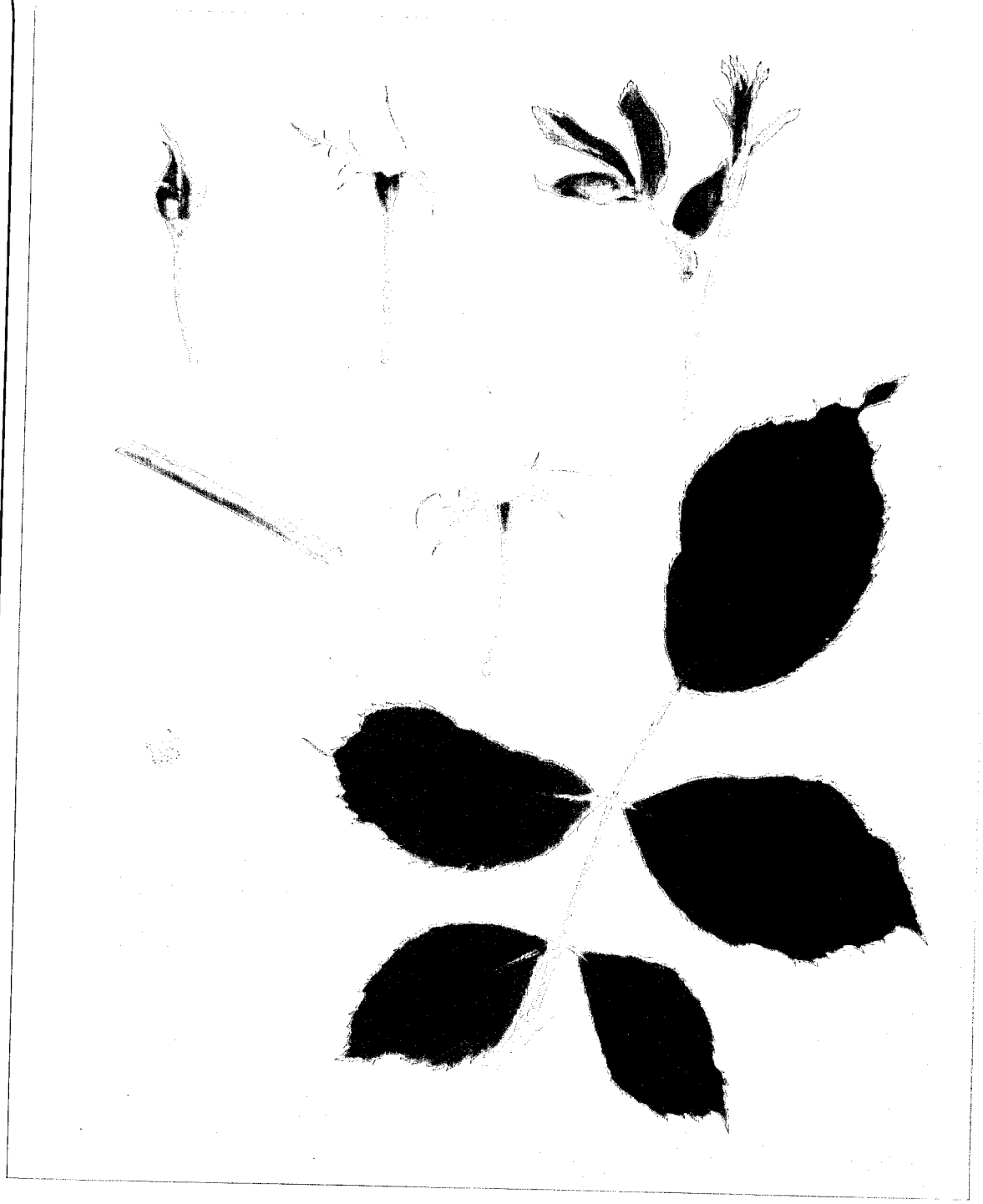
Inventor.
E. S. Boerner
By: Robbs & Robbs
Attorneys.

Patented Oct. 13, 1953

Plant Pat. 1,222

UNITED STATES PATENT OFFICE 1,222

ROSE PLANT

Eugene S. Boerner, Newark, N. Y., assignor to Jackson & Perkins Company, Newark, N. Y., a corporation of New York Application October 9, 1952, Serial No. 313,996

1 Claim. (Cl. 47—61)

The present invention relates to a new and distinct variety of rose plant of the large-flowered polyantha class, which was discovered by me as a sport of the variety known as "Demure" (Plant Patent No. 1065). The new sport was discovered by me in a block of greenhouse bench plants being grown under my direction and control for cut-flower purposes on property owned and controlled by my assignee-employer.

The parent variety "Demure" is characterized by its production of flowers which are Cameo Pink in general color tonality, and my attention was attracted to the new sport herein because of the fact that the flowers of the sport which occurred on one of the plants of "Demure" bore white flowers. Further observations, tests and asexual reproduction of the new sport showed that this white flower characteristic was fixed and comes true to form by asexual reproduction, thereby establishing that the sport was a true bud variation. In addition, I have found and established that the new sport has inherited other important characteristics from its parent variety, including the characteristics of prolific production of cut-flowers when grown under greenhouse conditions, long-lasting quality of the flowers which frequently will last from ten to twelve days, and exceptional hardiness when grown out-of-doors. The combination of these characteristics with the white-colored flowers of the type of the parent variety "Demure" definitely establishes the new sport as a new variety which is distinguished from its parent, as well as from all other varieties of its class, and makes it especially suitable for cut-flower production.

My new variety has been asexually reproduced in greenhouses at Newark, New York, by grafting on Manetti understocks, and also by budding in fields at both Newark, New York, and at Pleasanton, California, and all such reproductions have shown that the foregoing characteristics come true to form and are established and transmitted through succeeding propagations.

The accompanying drawing shows specimens of the flowers, stems and foliage of my new variety, with the flowers and foliage in different stages of development.

The following is a detailed description of my new variety, with color terminology in accordance with Ridgway's Color Standards and Nomenclature:

Parentage: Sport of "Demure."
Classification:
*Botanic.*—Large-flowered polyantha.
*Commercial.*—Floribunda.

*Flower*

(Observations made in a greenhouse at Newark, New York, in the early morning during the early part of the month of July.)

Blooming habit: Recurrent—continuous.
Bud:
*Size.*—Small.
*Form.*—Ovoid; is not affected by wet or hot weather.
*Color.*—When sepals first divide—Sea-foam Green, Plate 31. When petals begin to unfurl—White, Plate 53; lower half of the petal lightly overcast with Primrose Yellow, Plate 30. When half blown: inside of petals—White, Plate 53; reverse of petals—White, Plate 53.
*Sepals.*—Smooth edge; slightly branched; curl back when petals begin to unfurl. Color: inside—Clear Fluorite Green, Plate 32; outside—Chromium Green, Plate 32.
*Calyx.*—Color—Absinthe Green, Plate 31. Shape—funnel. Size—small. Aspect—smooth. Odor when rubbed—none.
*Peduncle.*—Length—short. Aspect—rough. Color — Absinthe Green, Plate 31. Strength—erect; slender.
*Opening.*—Opens up well; is not affected by adverse weather conditions.
Bloom:
*Size.*—Small; average size when fully expanded 2 inches to 2¼ inches.
*Borne.*—Several together and in irregular clusters.
*Stems.*—Medium length; normal strength.
*Form.*—When first open—cupped. Permanence—flattens.
*Petalage.*—Double (full but open center). Number of petals under normal conditions—30 to 35.
*Color.*—Center of flower—White, Plate 53. Outer petals—White, Plate 53. Base of petals (aiglet)—Pale Lumiere Green, Plate 17. Inside of petals—White, Plate 53. Reverse of petals—White, Plate 53. General tonality from a distance—White, Plate 53.
*Discoloration.*—General tonality at end of first day—White, Plate 53. Second day—White, Plate 53. Third day—White, Plate 53.
Petals:
*Texture.*—Leathery; is not affected by wet or hot weather.
*Appearance.*—Inside—satiny; outside—shiny.
*Form.*—Oval; slightly notched.

*Arrangement.* — Imbricated (regularly arranged shingle like).
*Petaloids in center.*—Few; small.
*Persistence.*—Drop off cleanly.
*Fragrance.*—Slight. Nature—tea (average hybrid tea scent).
*Lasting quality.*—On the plant—very long. As cut flower—very long.

*Genital organs*

Stamens, anthers: Small; many. Color—Chamois, Plate 30. Arrangement—regular around styles.
Stamens, filaments (threads): Short. Color—Pale Green Yellow, Plate 6.
Pollen: Color—Naphthalene Yellow, Plate 16.
Styles: Columnar; loosely separated; uneven length; short; thin.
Stigmas: Color—Pale Lumiere Green, Plate 17.
Ovaries: All enclosed in calyx.
Seeds: None.

*Plant*

Form: Bush.
Growth: Vigorous; branching.
Foliage: 5 to 7 leaflets.
*Size.*—Medium.
*Quantity.*—Normal abundance.
*Color.*—New foliage: upper side—Oil Green, Plate 5, lightly overcast with Oxblood Red, Plate 1; under side—Biscay Green, Plate 17, overcast with Oxblood Red, Plate 1. Old foliage: upper side—Varley's Green, Plate 18; under side—Bice Green, Plate 17.
*Shape.*—Oval pointed.

*Texture.* — Upper side — leathery. Under side—smooth.
*Ribs and veins.*—Ordinary.
*Edge.*—Serrated (saw-toothed).
*Serration.*—Double and single; sharp.
*Leaf stem.*—Color—Courge Green, Plate 17. Under side—prickles.
*Stipules.*—Medium length; bearded.

Wood:
*New wood.*—Color—Lettuce Green, Plate 5. Bark—smooth.
*Old wood.*—Color—Spinach Green, Plate 5. Bark—smooth.

Thorns:
*Thorns.*—Quantity—on main stalks from base—few; on laterals from stalk—none. Form—narrow base; short. Color when young—Begonia Rose, Plate 1. Position—irregular.
*Prickles and short needles.*—On main stalks and on laterals—none.

I claim:

A new and distinct variety of rose plant of the large-flowered polyantha class, substantially as herein shown and described, characterized particularly as to novelty by the white color of its flowers, by its prolific production of cut-flowers when grown under greenhouse conditions, by the long-lasting quality of its flowers, and by its hardiness when grown out-of-doors.

EUGENE S. BOERNER.

No references cited.